United States Patent [19]

Lottick

[11] Patent Number: 5,026,370
[45] Date of Patent: Jun. 25, 1991

[54] ELECTROCAUTERY INSTRUMENT

[76] Inventor: Edward A. Lottick, 41 Gershom Pl., Kingston, Pa. 18704

[21] Appl. No.: 881,750

[22] Filed: Jul. 2, 1986

Related U.S. Application Data

[63] Continuation of Ser. No. 663,091, Oct. 24, 1984, abandoned, Continuation-in-part of Ser. No. 443,517, Nov. 22, 1982, Pat. No. 4,552,143, Continuation-in-part of Ser. No. 242,746, Mar. 11, 1981, Pat. No. 4,370,980.

[51] Int. Cl.$^5$ .................................................. A61B 17/38
[52] U.S. Cl. .................................... 606/42; 606/45; 606/49; 606/52
[58] Field of Search .......... 128/303.1, 303.12, 303.13, 128/303.14, 303.15, 303.17, 303.18; 606/42, 45, 44, 51, 52

[56] References Cited

U.S. PATENT DOCUMENTS

| | | | |
|---|---|---|---|
| 164,183 | 6/1875 | Kidder | 128/303.1 |
| 371,664 | 10/1887 | Brannan | 128/303.1 |
| 595,573 | 12/1897 | MacGregor | 128/303.14 |
| 702,472 | 6/1902 | Pignolet | 128/303.1 |
| 1,071,978 | 9/1913 | White | 128/303.13 |
| 1,813,902 | 7/1931 | Bovie | 128/303.14 |
| 2,002,594 | 5/1935 | Wappler et al. | 128/303.14 |
| 2,012,937 | 9/1935 | Beuoy | 128/303.14 |
| 2,176,479 | 10/1939 | Willis | 128/303.13 |
| 2,249,894 | 7/1941 | Goldenstein | 128/303.13 |
| 2,888,927 | 6/1959 | Fozard | 128/303.13 |
| 3,100,489 | 8/1963 | Bagley | 128/303.17 |
| 3,234,356 | 2/1966 | Babb | 128/303.1 |
| 3,643,663 | 2/1972 | Sutter | 128/303.17 |
| 3,752,160 | 8/1973 | Billin | 128/303.17 |
| 3,789,831 | 2/1974 | Kopaniky et al. | 128/692 |
| 3,801,766 | 4/1974 | Morrison, Jr. | 200/157 |
| 3,878,348 | 4/1975 | German | 200/157 |
| 3,911,241 | 10/1975 | Jarrard | 128/303.17 |
| 3,938,527 | 2/1976 | Rioux et al. | 128/303.17 |
| 3,980,861 | 9/1976 | Fukunaga | 128/303.1 |
| 3,982,529 | 9/1976 | Sato | 128/641 |
| 4,005,714 | 2/1977 | Hiltebrandt | 128/303.17 |
| 4,032,738 | 6/1977 | Esty et al. | 128/303.13 |
| 4,034,761 | 7/1977 | Prater et al. | 128/303.14 |
| 4,041,952 | 8/1977 | Morrison, Jr. et al. | 128/303.13 |
| 4,076,028 | 2/1978 | Simmons | 128/303.13 |
| 4,174,714 | 11/1979 | Mehl | 128/303.13 |
| 4,213,460 | 7/1980 | Weiner | 128/303.1 |
| 4,367,744 | 1/1983 | Sole | 128/303.1 |
| 4,370,980 | 2/1983 | Lottick | 128/303.17 |
| 4,375,218 | 3/1983 | DiGeronimo | 128/303.17 |
| 4,418,692 | 12/1983 | Guay | 128/303.14 |
| 4,552,143 | 11/1985 | Lottick | 128/303.17 |

FOREIGN PATENT DOCUMENTS

| | | | |
|---|---|---|---|
| 305566 | 1/1952 | Denmark | 128/303.1 |
| 1803292 | 10/1968 | Fed. Rep. of Germany | 128/303.17 |
| 757933 | 10/1933 | France | 128/303.14 |
| 1536272 | 6/1967 | France | 128/303.17 |
| 575103 | 10/1977 | U.S.S.R. | 128/303.14 |
| 578972 | 11/1977 | U.S.S.R. | 128/303.14 |

OTHER PUBLICATIONS

"New Bipolar Forceps for Electrocoagulation", by Rosenberg, Plastic & Reconstructive Surgery, vol. 48, No. 4, 1964.
"Combined Diathermy Forceps and Scissors", by Stevenson; The Lancet; Oct. 24, 1959.

Primary Examiner—David Shay
Attorney, Agent, or Firm—Michael F. Petock

[57] ABSTRACT

An electrocautery instrument which is provided with a non-removable enclosed electrical switching mechanism. The entire switch assembly may be sealed from human contact by an insulating medium.

33 Claims, 2 Drawing Sheets

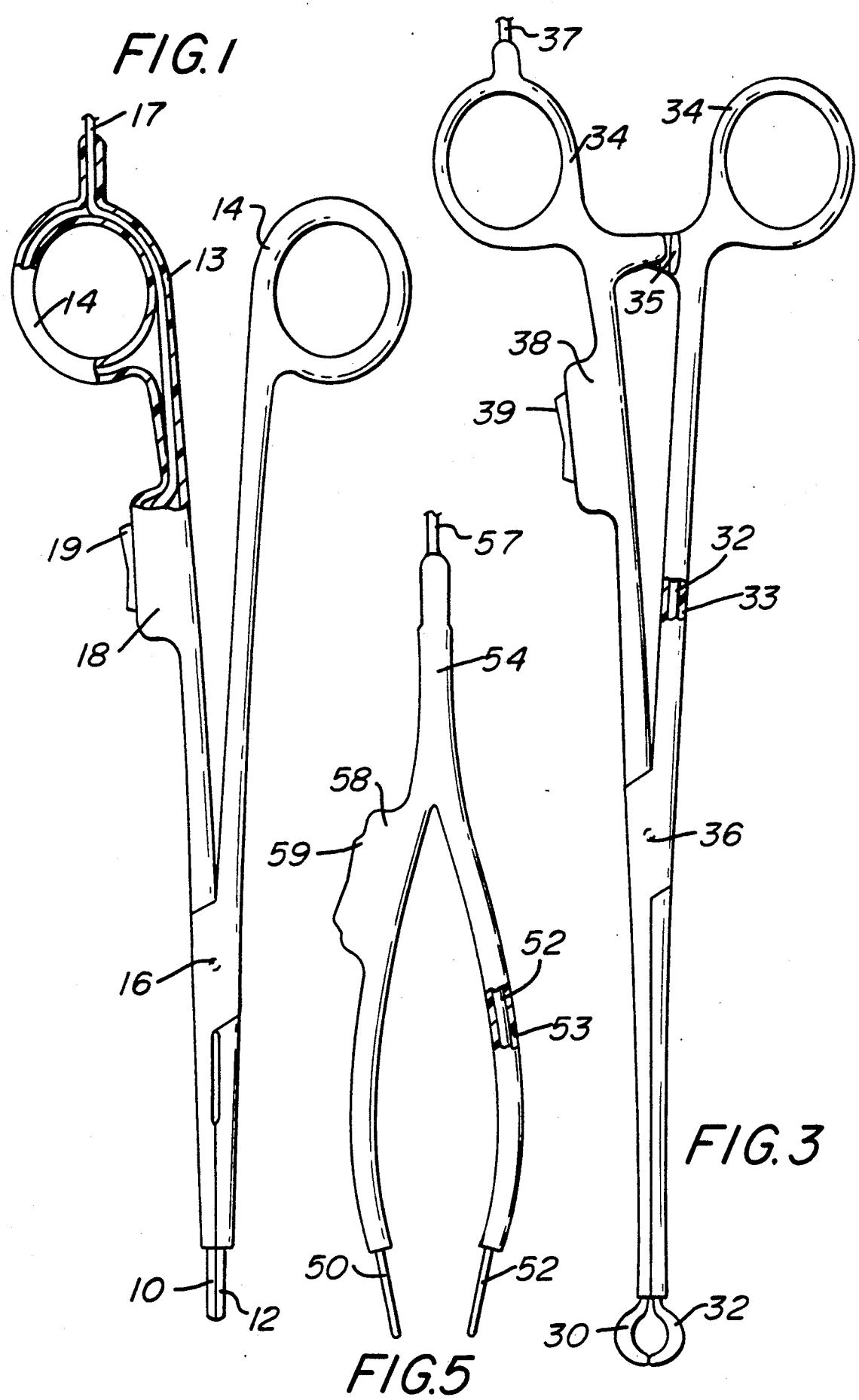

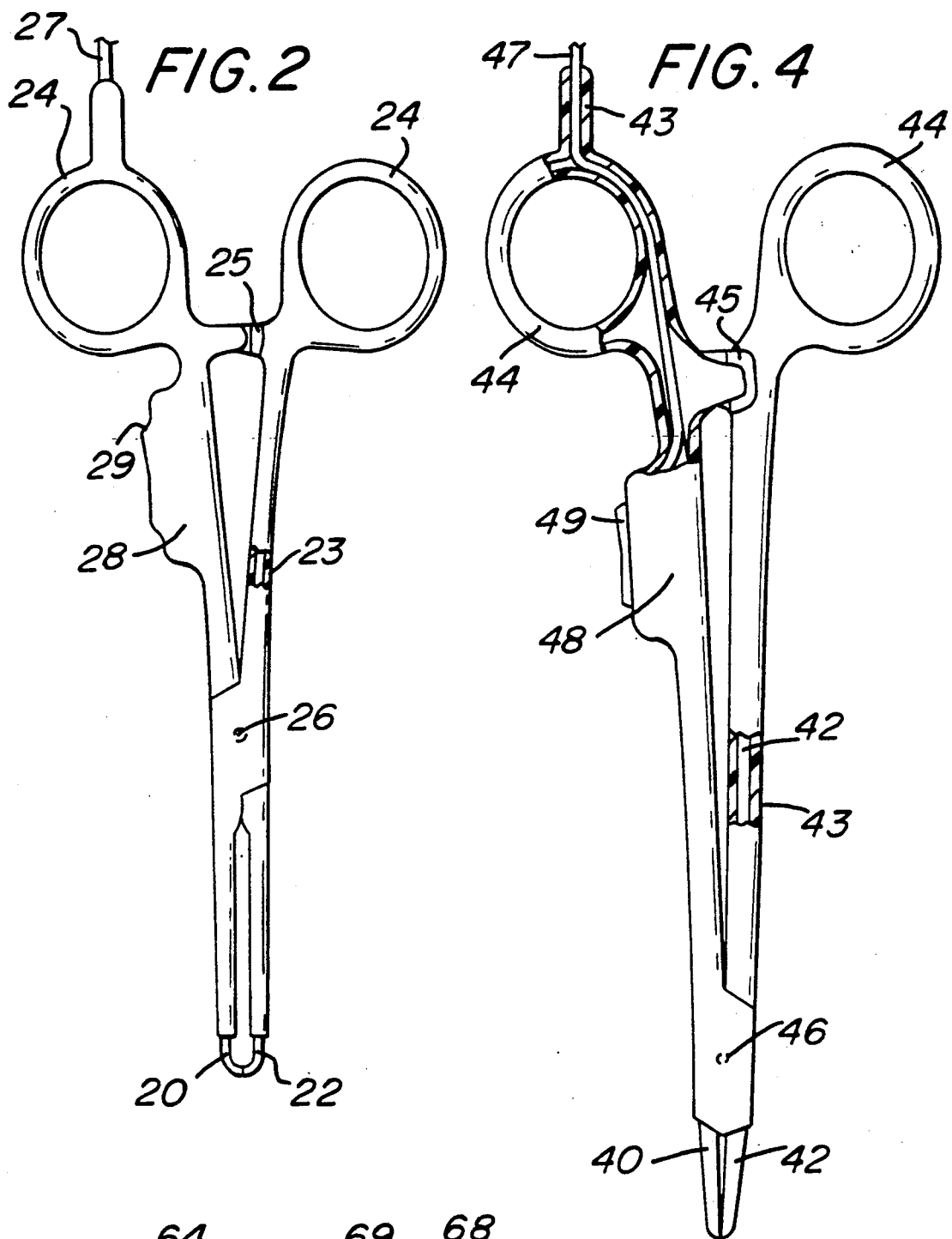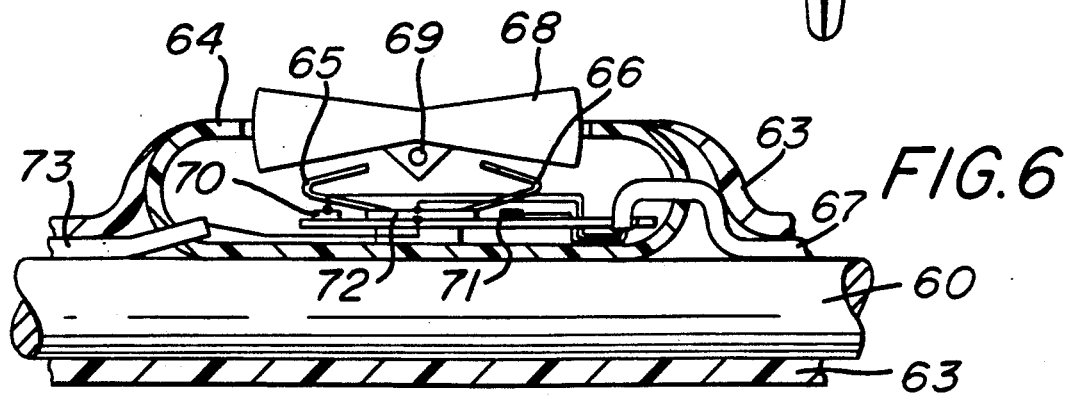

ELECTROCAUTERY INSTRUMENT

CROSS REFERENCE TO RELATED APPLICATIONS

This is a continuation application of application Ser. No. 663,091, filed Oct. 24, 1984, by the inventor herein and entitled "ELECTROCAUTERY INSTRUMENT", now abandoned.

Application Ser. No. 663,091 is a continuation-in-part application of U.S. patent application Ser. No. 443,517, filed Nov. 22, 1982, by the inventor herein and which is entitled REMOVABLE SWITCH ELECTROCAUTERY INSTRUMENTS, now U.S. Pat. No. 4,552,143; which in turn is a continuation-in-part application of U.S. patent application Ser. No. 242,746, filed Mar. 11, 1981 by the inventor herein and which is entitled ELECTROCAUTERY HEMOSTAT, now U.S. Pat. No. 4,370,980. The teachings of both of my two prior patents are incorporated herein by reference.

BACKGROUND OF THE INVENTION

The present invention is directed to electrocautery instruments which have at least two conductive members operable to engage tissue therebetween.

In the above-referred to co-pending application from which this is a continuation-in-part, a family of electrocautery instruments are described which are provided with a removable switch. Many significant advantages for those electrocautery instruments are described, particularly as the switch can be adapted to combine with conventional surgical instruments. More importantly, the extreme versatility in being able to connect various instruments, easily and efficiently, to the supply of electrical energy for rapid use on the surgical field is achieved. Finally, instruments may be replaced quickly when scraping or other cleaning of the electrocautery tip is necessary. The invention described therein is particularly suitable for use with scapels or scapel like instruments which are used for cutting or cauterizing, although other types of surgical instruments are disclosed therein.

Another form of electrocautery instrument is described in the above referred to patent application which has matured into U.S. Pat. No. 4,370,980. Described therein is an electrocautery and hemostatic clamping device, which provides for first and second pivoted members having mating jaws at one end and means for retaining the jaws in a predetermined clamped position. An electrical switch means is adapted to be releasably attached to one of the members to utilize the thus provided electrical potential to enable use of the instrument for cauterizing. The device is particularly suitable for use on larger blood vessels, where it is often times necessary to "pluck the bleeder" from the incision with a hemostat and then apply an electrocautery instrument to the bleeder.

While the advantages of the above-described devices are readily apparent, no single device is always ideal over every possible set of operating conditions and circumstances. There are some instances when reliability and safety are more important than any other factors. There is a particular need in certain surgical operations for a device which not only functions as an electrocautery instrument but which is capable of engaging tissue therebetween. In these particular circumstances, the device must be operable as a surgical instrument for the purpose that it was originally designed to perform. At the same time, it must be able to operate as an electrocautery instrument regardless of the position and/or operating condition of the instrument. Finally, the device should operate with a maximum degree of safety and reliability during the myriad of conditions which are found during surgical operations. More precisely, the device should be designed to apply the appropriate electrocautery treatment to the area which is intended for that treatment without any danger that the surgical personnel or the person be in any danger from unwanted or inadvertent contact with electrical current at any time other than that which is intended. In addition, because often times the timing of the electrocauterization can be of primarily importance during a surgical procedure, it is absolutely essential that the switch operate immediately upon demand and without fail each and every time that it is called upon to operate the electrocautery portion of the device.

Many times, these two features of safety and reliability are the premium features which must be provided if the device is to be in any way usable in the operating room.

SUMMARY OF THE INVENTION

In accordance with the present invention, an electrocautery instrument is provided which is both highly reliable and extremely safe. The device includes at least two conductive members which are operable to engage tissue therebetween. Handle means are provided for positioning the members and the handle means have a conductive portion which is operably connected to the two conductive members. Also, there is a connection means for connecting to a source of electrical energy and this connection means is affixed to the handle and is in electrically insulated contact with the handle. Switch means are affixed to the handle and are electrically interposed between the conductive portion of the handle and the connecting means. This permits selective control of the flow of electrical energy from the source to the conductive members. Finally, insulating means are provided which insulate the handle, the switch and the connecting means from an operator while at the same time exposing at least a tissue engaging portion of the conductive members for engaging the tissue therebetween.

The switch which is utilized in this invention may in one embodiment include a movable electrical control member having a non-conductive portion exposed for movement by an operator. In another embodiment, the switch means may include a movable electrical control member enclosed by the insulating means and movable through the insulating means by pressure exerted thereon. The insulating means would, in either case, be provided to protect the operator at all times since the movable electrical control member is either covered by the insulating means or non-conductive in and of itself.

The switch itself may further include means for connecting to one of two or more different electrical potentials, so as to provide optional voltages to the electrocautery function of the device. In one embodiment, the switch means may include a movable member which is biased in a first condition wherein electrical current does not flow through the switch, such that the movable member may be positioned to be moved against the bias by operator finger pressure to a second condition wherein electrical energy does flow through the switch means.

One highly suitable form of the connection means would comprise an insulated electrical wire affixed to the handle means by the insulating means such that the wire has electrical contact with the switch means. For optimum reliability, the switch means which is fixedly mounted on the handle and has at least terminal making electrical contact with the conductive portion of the handle. The switch has at least one condition permitting flow of electrical energy from the connection means to the conductive members and at least one other condition which prevents said flow of electrical energy. Thus the switch is able to control the flow of electrical energy, and, in fact, is operable to selectively control the flow independent of the relative position of the conductive members with respect to each other. This independence from the relative position of the conductive members also includes an independence from whether or not the conductive members have any tissue engaged therebetween.

The present invention is admirably suited to a wide variety of electrocautery instruments. Typically, various devices such as hemostats, tweezers, forceps, Allis clamps and Babcock clamps and the like may be modified according to the principles of the present invention to provide devices which are both very reliable and exceedingly safe for operation.

As will be explained in greater detail hereinafter, the safety and reliability of devices embodying the principles of the present invention results from the interconnection of the various components in the manner described herein. A switch which is fixedly mounted on a handle and connected firmly to both the insulated electrical wire of a connection means and a portion of the handle such that all of the instrument covered with an insulating means except a tissue engaging portion of the two conductive members is safe and reliable and can be trusted to perform its function in the operating theater.

BRIEF DESCRIPTION OF THE DRAWINGS

FIG. 1 is a side elevational view showing an electrocautery instrument in accordance with the present invention, partially in section.

FIG. 2 is an elevational view of an electrocautery Allis clamp showing another embodiment in accordance with the present invention.

FIG. 3 is an elevational view of an electrocautery Babcock clamp in accordance with the present invention.

FIG. 4 is an elevational view of an electrocautery hemostat in accordance with the present invention.

FIG. 5 is an elevation view of an electrocautery tweezer or forceps in accordance with the present invention.

FIG. 6 is a cross-sectional view of a portion of an electrocautery device illustrating the electrocautery switch arrangement of a preferred embodiment in accordance with the present invention.

DETAILED DESCRIPTION OF THE PREFERRED EMBODIMENTS

Referring now to the drawings, wherein like numerals indicate the like elements, there is shown in FIG. 1 one of a family of electrocautery instruments which comprise the present invention. As shown in this FIG., a first conductive member 10 and second conductive member 12 are operably connected to engage tissue therebetween. Handle means 14 are positioned on both conductive members 10 and 12 for positioning the members which, in this example, are centered about pivot 16.

Normally, the entire instrument of conductive members 10 and 12 and the handle 14 are made from the same conductive metal so that the handle means has a conductive portion operably connected to the conductive members. In other embodiments where a non-conductive handle might be employed, those handle means are provided with a conductive portion operably connected to the conductive members. A connection means 17 for connection to a source of electrical energy (not shown) is affixed to the handle 14 and is in electrically insulated contact therewith. Typically, the connection means 17 may be an insulated electrical wire.

A switch means 18 is affixed to the handle and is electrically interposed between the conductive portion of the handle 14 and the connection means 17 to selectively control the flow of electrical energy from the source to the conductive members 10 and 12. As shown in this embodiment, the switch means 18 includes a movable electrical control member 19 which has a non-conductive portion exposed for movement by an operator. The entire instrument, except for a tissue engaging portion of the conductive members 10 and 12, is covered with an insulation means 13 to insulate the handle, switch means and the connection means from an operator who would be using the instrument.

As shown in FIG. 2, an Allis clamp having a conductive member 20 and 22 operably able to engage the tissue therebetween. Handle means 24 operate to position the members and operate the instrument about pivot 26. Locking means 25 allows the device to be clamped in various positions as in conventional devices.

The connection means 27 provides a source of electrical energy to switch 28, and the entire device including the handles 24 and switch 28, as well as substantial portions of the conductive members 22 and 20 are covered by insulation means 23. The switch means 28 includes a movable electrical control member 29 which is enclosed by the insulating means 23 but is movable through the insulating means by pressure exerted thereon.

In FIG. 3, a Babcock clamp embodying the principles of this invention is provided wherein the conductive members 30 and 32 pivot about pivot 36 through the use of handle 34. Again locking means 35 is adapted to provide various locked positions of the movable conductive members 30 and 32. Connection means 37 provides a supply of electrical energy to switch 38. Switch 38 includes a movable electrical control member 39 which has a non-conductive portion exposed for movement by the operator. Again, the insulation in 33 covers all of the device which might be exposed to the operator of the instrument during surgery, so that the conductive members 30 and 32 may be employed to engage tissue therebetween. The operability of the switch permits flow of the current to cause an electrocautery contact with the tissue upon operation of the switch by the surgical personnel.

The hemostat shown in FIG. 4 includes the conductive members 40 and 42 which are attached to the handle 44 and are pivoted about pivot 46. The connection means 47 comprises an electrical wire which is insulated and which is attached to the handle means and operably connected to the switch means 48. The movable electrical control member in 48 is positioned with a non-conductive portion exposed for movement by an operator. Locking means 45 allows the hemostat to be clamped as in conventional designs.

In another embodiment of the present invention, a tweezer or forceps is shown with conductive members 50 and 52 positioned about a handle 54. Attached thereto is a connection means 57 for a source of electrical energy. The connection means 57 is in electrically insulated contact with the handle 54. Electrically interposed between the conductive portion of the handle 54 and the connection means 57 is a switch means 58 which includes a movable electrical control member 59. The switch, including the control member 59, as well as the handle 54, of the connection means 57 and substantially all of the conductive members 50 and 52 are covered or enclosed by insulating means 53 in order insulate all of these elements from the operator while exposing at least a tissue engaging portion of the conductive members 50 and 52.

In each of the foregoing electrocautery instruments, an electrically insulating covering has been shown. In FIG. 1, the connection means 17, which has been described as an insulated electrical wire, passes along the handle 14 to which it is mounted and into switch 18. The insulating means 13 completely encloses the wire 17 and the handle 14 so as to permanently mount the electrical wire 17 on the handle 14. Thus, whether the switch is of the type shown in FIG. 1 with the exposed non-conductive movable electrical control member 19 or the movable electrical control member 59 as shown in FIG. 5 and enclosed by the latex, there is no electrically conductive elements exposed to the operator. The only conductive portion exposed is the tissue engaging portion of the conductive members, such as 50 and 52 in FIG. 5.

As shown in FIG. 6, the details of a particular switch means are shown. The conductive member 60 of an electrocautery instrument is shown. This conductive member 60 might be any of the conductive members shown in the previously described instruments or in other instruments, as the function of this portion of the device is to provide for electrical conduction to the exposed tips of the electrocautery instrument. The switch itself includes a housing 64. The switch is connected electrically to the source of electrical energy be connection means 67 which is an insulated wire mounted on the device. Spring elements 65 and 66 are positioned in electrical contact with electrical contacts 70, 71 and 72. Movement of the movable electrical control members 68 about pivot 69 in either direction will cause the movable members 68 to depress either spring 65 or spring element 66. If, by way of example, the left hand portion of movable member 68 is depressed so that it contacts spring element 65, electrical contact between electrical contact 70 and electrical contact 72 is made and electrical energy is allowed to flow from the connection means 67 to the electrical contact 73 which is in contact with the conductive member 60. In this position, electrical energy flows to the portions of the conductive members which form the tissue engaging portions thereof. The switch 64, the connection means 67 and the conductive member 60, as well as the electrical contact 73 and all other portions of the switch are protected by insulating means 63. The movable control member 68 is, of course, made from a non-conductive material so that its contact with either spring element 65 or spring element 66 will not cause any electrical contact with the operator who is operating the switch.

In the embodiment shown in FIG. 6, two spring elements 65 and 66 are shown so that the switch means is provided with means for connecting one of two different electrical potentials to the conductive members. Typically, one electrical potential would be substantially more moderate than the other so as to provide for reasonable control by the operator.

Other variations of this structure are within the scope of the present invention, including the mounting of more than one switch or the use of switches which contain only one electrical potential contact.

Various electrical switches may be employed according to the present invention with various surgical instruments which are used for grasping or clamping tissue therebetween.

It is contemplated that many of the conventional surgical instruments may be adapted to the present invention by modification as described herein. Typically, a hemostat or other surgical instrument might have an appropriate switch attached thereto along with an insulated wire which may be connected to a source of electrical energy. The insulated wires attached into the switch such that one operable position of the switch will permit flow of current through the switch to the conductive portion of the surgical instrument. Then the entire surgical instrument, including the handle, switch, and connection means is dipped in a bath of latex or other insulating material at a temperature below that which would cause damage to the switch or melt the electrical connection insulation. The entire device may be dipped or the tissue engaging portions of the conductive members may be held out of the latex bath so that they may operate as an electrocautery device when used to engage tissue therebetween. If the entire device is dipped, clearly, the tissue engaging portion must be exposed by an additional step in the manufacture of the instrument.

In view of the above, the present invention may be embodied in other specific forms without departing from the spirit or essential attributes thereof, and, accordingly, reference should be made to the appended Claims, rather than to the foregoing Specification as indicating the scope of the invention.

I claim:

1. An electrocautery instrument, comprising:

a surgical instrument made of a conductive material;

said conductive surgical instrument being comprised of a pair of members pivotally mounted together at a point between the ends of said members, each member having a tissue engaging portion at one end and a handle portion at the opposite end;

an electrical switch having a non-conductive housing and a first and a second electrical contact therein and a control member for operating said contacts mounted to said housing and positioned such that it is movable to control said contacts;

an electrically conductive wire insulated from said conductive members, said conductive wire being electrically connected to said first electrical contact of said switch and the other end of said electrical wire being adapted to be connected to a source of electrical energy;

said second electrical contact of said switch being electrically connected to one of the conductive member of said surgical instrument enabling current flow through said conductive member when said switch is engaged to enable current flow through a tissue;

said non-conductive housing of said switch being mounted on said one member of said surgical instrument;

said electrically conductive wire, with one end of the conductive wire connected to said first electrical contact of said switch, running along a portion of said one of said pair of said electrically conductive surgical instrument members and insulated therefrom; and a layer of insulating material covering said switch housing, said wire running along said portion of one of said instrument members and at least a portion of said conductive surgical instrument, but not said tissue engaging ends of said members.

2. An electrocautery instrument in accordance with claim 1 wherein said layer of insulating material is comprised of latex.

3. An electrocautery instrument in accordance with claim 1 wherein said movable control member is comprised of a non-conductive material.

4. An electrocautery instrument in accordance with claim 1 wherein said layer of insulating material covers surfaces of the movable control member which project from said switch housing and covers said switch housing, said wire running along said portion of one of said instrument members and all of said conductive surgical instrument except for said tissue engaging ends of said members.

5. An electrocautery instrument in accordance with claim 1 wherein said switch is provided with means for connecting one of two different electrical potentials to said conductive members of said surgical instrument.

6. An electrocautery instrument in accordance with claim 1 wherein said switch control movable member is biased in a first condition wherein said electrical current does not flow through said switch, said movable control member being positioned to be moved against said bias by operator finger pressure to a second condition wherein electrical current does flow through said switch.

7. An electrocautery instrument in accordance with claim 1 wherein said electrical switch is operable to selectively control the flow of electrical energy from said source to said conductive members independent of the relative position of the conductive members with respect to each other.

8. An electrocautery instrument in accordance with claim 1 wherein said electrical switch is operable to selectively control said flow of electrical energy independent of whether or not said conductive members have any tissue engaged therebetween.

9. An electrocautery instrument in accordance with claim 1 wherein said instrument is a hemostat.

10. An electrocautery instrument in accordance with claim 1 wherein said switch of said instrument includes means for producing a larger and a smaller potential, one relative to the other, at the tissue engaging portions of said members, wherein the lower potential may be used with said first electrical potential for coagulation and said larger potential may be used with said second electrical potential for cutting.

11. An electrocautery instrument in accordance with claim 1 wherein said instrument is selected from the group of Allis clamps and Babcock clamps.

12. An electrocautery instrument in accordance with claim 1 wherein said handle portion of each member is comprised of a ring.

13. An electrocautery instrument, comprising:

an electrically conductive surgical instrument, said surgical instrument including at least two conductive members pivotally mounted together at a point between the ends of said members and provided with tips at one end of each member operable to engage tissue therebetween;

said surgical instrument including handle means provided for said two conductive members for positioning said members;

connection means for connection to a source of electrical energy including an insulated electrical wire affixed along at least a portion of said handle means;

switch means affixed to one of said conductive members and having at least one terminal making electrical contact with said one of said conductive members and having electrical contact with said electrical wire of said connection means, said switch means including a movable member biased in a first condition wherein electrical current does not flow through said switch means, said movable member being positioned to be moved against said bias by operator finger pressure to a second condition wherein electrical current does flow through said switch means from said connection means to said conductive members; and insulating means comprising a layer of non-conductive material covering and insulating said handle means of said surgical instrument, at least a portion of said switch means and said insulated wire affixed along said portion of said handle means thereby insulating an operator while exposing at least a tissue engaging portion of said conductive members for engagement of said tissues and enabling electrical current flow through said tissues when current flows through said switch means.

14. An electrocautery instrument in accordance with claim 13 wherein said movable electrical control member of said switch means is provided with a non-conductive portion extending beyond said insulating layer and exposed for movement by an operator.

15. An electrocautery instrument in accordance with claim 13 wherein said movable member is covered by said non-conductive layer and is adapted to move when subjected to operator pressure against said non-conductive layer covering said movable member.

16. An electrocautery instrument in accordance with claim 13 wherein said switch means is provided with means for connecting one of two different electrical potentials to said conductive member.

17. An electrocautery instrument in accordance with claim 13 wherein said switch means is operable to selectively control the flow of electrical energy from said source to said conductive member independent of the relative position of the conductive members with respect to each other.

18. An electrocautery instrument in accordance with claim 13 wherein said switch means is operable to selectively control said flow of electrical energy independent of whether or not said conductive members has any tissue engaged therebetween.

19. An electrocautery instrument in accordance with claim 13 wherein said instrument is a hemostat.

20. An electrocautery instrument in accordance with claim 13 wherein said switch means of said instrument includes means for producing a larger and a smaller potential, one relative to the other, at the tissue engaging tips of said members, wherein the lower potential may be used with said first electrical potential for coagulation and said larger potential may be used with said second electrical potential for cutting.

21. An electrocautery instrument in accordance with claim 13 wherein said instrument is selected from the group of Allis clamps and Babcock clamps.

22. An electrocautery instrument in accordance with claim 13 wherein said handle means includes rings formed at the ends of said conductive members of said surgical instrument opposite the ends of the members provided with the tips for engaging tissue.

23. An electrocautery instrument, comprising:
a first and a second pivoted members pivoted at a point between the ends of said members, said members being comprised of a conductive material;
said first and second pivoted members being provided with mating jaws at one end;
said first and second pivoted members being provided with handle means at a predetermined distance from said point at which said members are pivoted and on the other side of the pivot from said jaws;
an electrical switch means affixed along one of said pivoted members between said pivot point and the handle means of said member, said switch means including a non-conductive housing, a first and second electrical contacts mounted within said housing and a movable control member for operating said contacts mounted to said housing, said movable control member being operable to enable an electrical current flow through at least one of said conductive members and tissue;
an electrically conductive wire provided with insulation over said conductive wire, said conductive wire being electrically connected to one of said contacts of said switch means and the other end of said electrical wire being adapted to be connected to a source of electrical energy;
said insulated electrically conductive wire running from said switch housing along a portion of one of said pivoted members and along at least a portion of said one of said pivoted members' handle means; and
a layer of insulating material covering said switch housing, at least a portion of said insulated wire running along said portion of one of said pivoted members and at least said portion of the pivoted member along which said wire runs, at least a portion of the other of said pivoted members and the handle means of both said pivoted members but said jaws of said members being exposed without said layer of insulating material.

24. An electrocautery instrument in accordance with claim 23 wherein said layer of insulating material is comprised of latex.

25. An electrocautery instrument in accordance with claim 23 wherein said movable control member is comprised of a non-conductive material.

26. An electrocautery instrument in accordance with claim 23 wherein said layer of insulating material covers surfaces of the movable control member which project from said switch housing and covers said switch housing, said insulated wire running along said portion of one of said instrument members and all of said conductive surgical instrument except for said tissue engaging ends of said members.

27. An electrocautery instrument in accordance with claim 23 wherein said switch means is provided with means for connecting one of two different electric potentials to said conductive members of said surgical instrument.

28. An electrocautery instrument in accordance with claim 23 wherein said switch control movable member is biased in a first condition wherein said electrical current does not flow through said switch, said movable control member being positioned to be moved against said bias by operator finger pressure to a second condition wherein electrical current does flow through said switch.

29. An electrocautery instrument in accordance with claim 23 wherein said switch means is operable to selectively control the flow of electrical energy from said source to said conductive members independent of the relative position of the conductive members with respect to each other.

30. An electrocautery instrument in accordance with claim 23 wherein said switch means is operable to selectively control said flow of electrical energy independent of whether or not said conductive members have any tissue engaged therebetween.

31. An electrocautery instrument in accordance with claim 23 wherein said instrument is a hemostat.

32. An electrocautery instrument in accordance with claim 23 wherein said instrument is selected from the group of Allis clamps and Babcock clamps.

33. An electrocautery instrument in accordance with claim 23 wherein said handle means includes a ring on each pivoted member.

* * * * *

UNITED STATES PATENT AND TRADEMARK OFFICE
CERTIFICATE OF CORRECTION

PATENT NO. : 5,026,370

DATED : June 25, 1991

INVENTOR(S) : Edward A. Lottick

It is certified that error appears in the above-identified patent and that said Letters Patent is hereby corrected as shown below:

Column 5, line 42, delete "be" and insert --by--.

Signed and Sealed this

Twenty-second Day of December, 1992

Attest:

DOUGLAS B. COMER

Attesting Officer

Acting Commissioner of Patents and Trademarks